United States Patent
Baumstark

(10) Patent No.: US 11,433,255 B2
(45) Date of Patent: Sep. 6, 2022

(54) APPLICATOR FOR INTRAOPERATIVE RADIOTHERAPY

(71) Applicant: Carl Zeiss Meditec AG, Jena (DE)

(72) Inventor: Helge Baumstark, Neresheim (DE)

(73) Assignee: Carl Zeiss Meditec AG, Jena (DE)

( * ) Notice: Subject to any disclaimer, the term of this patent is extended or adjusted under 35 U.S.C. 154(b) by 255 days.

(21) Appl. No.: 16/587,030

(22) Filed: Sep. 29, 2019

(65) Prior Publication Data

US 2020/0101316 A1 Apr. 2, 2020

(30) Foreign Application Priority Data

Sep. 28, 2018 (DE) ...................... 10 2018 216 760.5

(51) Int. Cl.
*A61N 5/10* (2006.01)
*A61N 5/06* (2006.01)

(52) U.S. Cl.
CPC ......... *A61N 5/1001* (2013.01); *A61N 5/1078* (2013.01); *A61N 2005/0643* (2013.01); *A61N 2005/1089* (2013.01)

(58) Field of Classification Search
CPC ...... A61N 5/10–1084; A61N 2005/1085–1098
See application file for complete search history.

(56) References Cited

U.S. PATENT DOCUMENTS

| | | |
|---|---|---|
| 4,259,583 A | 3/1981 | Albert |
| 2005/0240073 A1* | 10/2005 | Apffelstaedt ........ A61N 5/1015 600/2 |
| 2008/0009730 A1 | 1/2008 | Warlick et al. |
| 2009/0234176 A1 | 9/2009 | Lebovic et al. |
| 2011/0105822 A1 | 5/2011 | Roeder |

(Continued)

FOREIGN PATENT DOCUMENTS

| | | |
|---|---|---|
| EP | 1281348 A3 | 2/2003 |
| EP | 1135699 B1 | 8/2004 |
| EP | 2268360 A2 | 1/2011 |

(Continued)

OTHER PUBLICATIONS

European Search Report dated Feb. 26, 2020 of European counterpart application No. EP 19198175 and English-language translation thereof.

(Continued)

*Primary Examiner* — Thaddeus B Cox
(74) *Attorney, Agent, or Firm* — Falk Ewers; Ewers IP Law PLLC

(57) ABSTRACT

An applicator for intraoperative radiotherapy with low-energy X-ray radiation includes an applicator body, an air-permeable outer surface with a circumferential outer face and with a distal end, a receiving device which is arranged at a proximal end and with which the applicator can be secured to an X-ray irradiation device, and an inner recess which has an opening at the proximal end and into which an X-ray radiation source is insertable. The applicator has a solid porous structure on its outer surface which provides the air-permeable outer surface with a rigid shape. The solid porous structure forms a continuous air-permeable channel structure which is connected in an air-conducting manner to the proximal end of the applicator.

11 Claims, 1 Drawing Sheet

(56) References Cited

U.S. PATENT DOCUMENTS

2015/0265462 A1    9/2015    LePivert

FOREIGN PATENT DOCUMENTS

| WO | 9839063 A1 | 9/1998 |
| WO | 2006047112 A2 | 5/2006 |
| WO | 2006050047 A3 | 5/2006 |
| WO | 2007108854 A2 | 9/2007 |
| WO | 2009108909 A1 | 9/2009 |
| WO | 2009111060 A2 | 9/2009 |
| WO | 2010060097 A2 | 5/2010 |
| WO | 2014137530 A1 | 9/2014 |
| WO | 2015158397 A1 | 10/2015 |

OTHER PUBLICATIONS

Office Action issued in German Patent Application No. DE 10 2018 216 760.5 (from which this application claims priority), dated Jun. 5, 2019 and English language translation thereof.

* cited by examiner

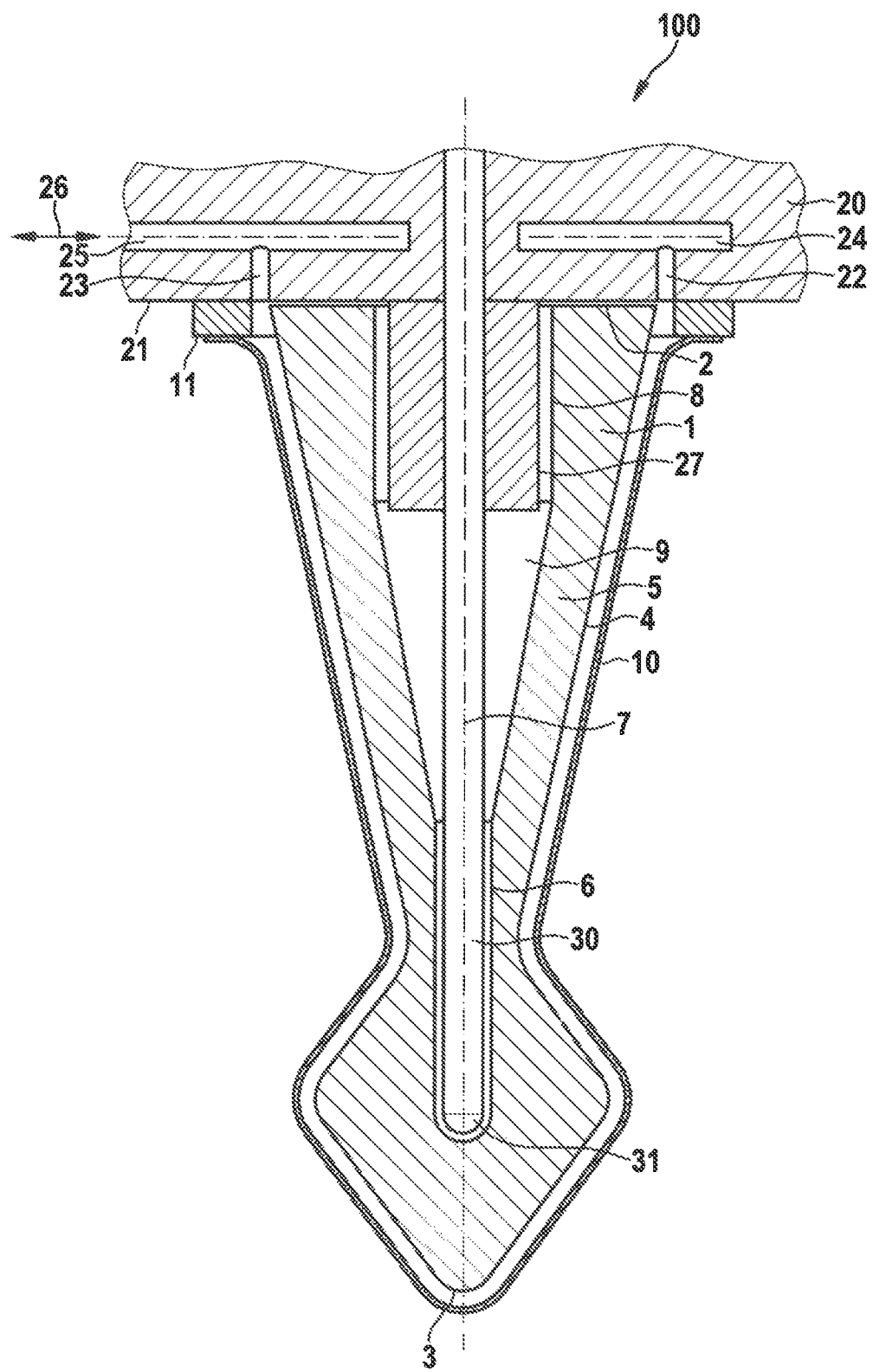

APPLICATOR FOR INTRAOPERATIVE RADIOTHERAPY

CROSS REFERENCE TO RELATED APPLICATIONS

This application claims priority to German patent application DE 10 2018 216 760.5, filed Sep. 28, 2018, the entire content of which is incorporated herein by reference.

TECHNICAL FIELD

The disclosure relates to an applicator for intraoperative radiotherapy with low-energy X-ray radiation.

BACKGROUND

In intraoperative radiotherapy, applicators are used which are arranged on an irradiation device. The irradiation device includes an X-ray source with an attachment point for an applicator. Arranged at the attachment point is an elongate tube whose distal end forms the X-ray source. An electron beam strikes a heavy-metal target, typically a gold target, which is arranged at the distal end of the tube, such that X-ray radiation is generated when the electron beam strikes the heavy metal.

At the attachment point of the irradiation device, a sleeve-shaped applicator is arranged, in the interior of which the tube with the X-ray source is arranged. The applicator is made from a radioparent material and is adapted in its outer geometry to a body opening or to the shape of a body opening created by surgery. The applicator can be chosen according to the nature and size of a body opening. Applicators can be used in different shapes and sizes depending on the particular case.

The applicator and the X-ray source arranged inside the applicator can be inserted into the body opening of a patient. The X-ray source can there generate X-ray radiation for therapeutic purposes, for example for irradiating a tumor. Since the applicator is invasive, i.e., is introduced into the tissue region of a body, low-energy radiation is sufficient for treating the body tissue. In this application, low-energy X-ray radiation is defined as radiation generated by an electron beam, with a kinetic energy of at most 100 keV, impacting the heavy-metal target, typically a gold target.

The body tissue is kept at a distance from the X-ray source by the applicator in order to effect uniform irradiation and/or to avoid a locally excessive X-ray dose in the direct environment of the X-ray source.

Applicators come into contact with body tissue during use. Therefore, the applicators have to be disposed of or sterilized after being used. After a limited number of re-sterilization cycles, the applicator is finally no longer usable and has to be discarded.

SUMMARY

It is an object of the disclosure to provide an improved applicator for intraoperative radiotherapy, with which applicator the number of uses can be increased.

The object is achieved by an applicator for intraoperative radiotherapy with low-energy X-ray radiation as described herein. The object is also achieved by a method for applying a sterile sleeve to an applicator as described herein.

According to an aspect of the disclosure, an applicator for intraoperative radiotherapy with low-energy X-ray radiation includes an applicator body, an outer surface with a circumferential outer face and with a distal end, a receiving device which is arranged at a proximal end and with which the applicator can be secured to an X-ray irradiation device, and an inner recess which has an opening at the proximal end and into which an X-ray radiation source is insertable.

The applicator has a solid porous structure on its outer surface, i.e., a structure which results in a rigid shape of the outer surface of the applicator with a precisely defined irradiation geometry. It is inherent that such a precisely defined irradiation geometry allows a very precise prediction and specification of a radiation dose acting on the body tissue to be treated. The solid porous structure forms a continuous air-permeable channel structure which is connected in an air-conducting manner to the proximal end of the applicator.

An applicator is a shaping application part for intraoperative radiotherapy with low-energy X-ray radiation.

The outer surface is defined as the surface of the applicator body on its circumferential region and at its distal end. A proximal end of the applicator body is configured to be secured to an X-ray irradiation device and, for this reason, has a shape configured for a defined positioning and fixing on the X-ray irradiation device. When the applicator is secured to the X-ray irradiation device, a region of the proximal end bears on the X-ray irradiation device. This bearing region is not regarded as an outer surface.

The applicator has an inner recess or a cavity. The recess or the cavity has an opening at the proximal end. The applicator is sleeve-shaped. An X-ray radiation source is thus insertable, through the opening at the proximal end of the applicator, into the recess or the cavity of the applicator. The X-ray radiation source includes a tube, at the distal end of which a radiation source is formed. The radiation source is thus arranged inside the applicator.

The applicator has a solid porous structure on its outer surface, wherein the solid porous structure forms a continuous air-permeable channel structure which is connected in an air-conducting manner to the proximal end of the applicator, such that air can be conducted from the entire outer surface to the proximal end of the applicator. An air stream can flow in both directions. Air can be aspirated out of the channel structure or blown in.

In this application, a porous structure is understood as a solid but air-permeable material structure which is provided with pores, holes, channels or cavities. The pores, holes, channels or cavities are connected to one another in an air-permeable manner, such that a branched system of multiple air channels is formed that are connected in an air-conducting manner to the proximal end of the applicator. In this way, an air stream can be formed from each region of the outer surface to the proximal end of the applicator. The term porosity is defined as a geometric property and represents, as measured variable, the ratio of a hollow volume to the total volume of the region of the applicator defined as porous. It will be noted at this point that a possibly colloquial understanding of the term "porous", which would describe an unstable material property, is not covered here by the term "porous".

A porous structure describes a functional air-conducting structure which extends from the outer surface into a depth region. The porous structure is therefore a functionally defined structure and thus differs from a surface roughness that results randomly from a type of manufacturing.

The pores, holes, channels or cavities are very small in relation to the size of the applicator and have very little or no influence on the outer geometry of the applicator.

The porous surface structure relates to the entire region of the outer surface, although a region at the proximal end of the applicator may have a surface that is not porous.

The applicator can be prepared individually for one use. Individual production for one patient is also conceivable. The applicator can have any desired outer contour.

Air can be aspirated or blown out through the functional porous surface structure of the outer surface of the applicator. In this way, the applicator can exert a force on another element, which can be fitted between the applicator and a tissue region. An example of a further element may be a shaped part, having a thin wall, or a film.

In this way, the applicator for intraoperative radiotherapy with low-energy X-ray radiation can be made available for a large number of uses. By virtue of its functional design, the applicator can apply a suction force or a pressure force to an element that comes into contact with a tissue region and is arranged between the applicator and the tissue. Thus, the applicator itself no longer comes into direct contact with a tissue region. Therefore, the applicator may be subject to less stringent demands as regards biocompatibility, sterilizability and temperature resistance. An applicator can be used more often. The number of uses, or the frequency of use, can be increased.

In one exemplary embodiment of the disclosure, the solid porous structure is formed by a fine channel structure arranged on the outer surface of the applicator.

A channel structure can be arranged directly on the surface. Thus, an air-conducting and structured outer surface can be applied at a later stage to an applicator. A fine channel structure is understood as a channel structure with a channel width of up to 3 millimeters (mm). In one exemplary embodiment, the channel width is configured to be increasing toward the proximal end.

In one exemplary embodiment of the disclosure, channels running from the proximal end to the air-permeable outer surface are arranged inside the applicator body, such that the air-permeable outer surface of the applicator is connected to the proximal end in an air-conducting manner.

To make available greater volumetric flows, channels can also be provided inside the applicator body. These channels can, for example, be introduced into the applicator by bores. The air flow can thus be optimized, and a uniform air flow can be obtained over the entire outer surface.

In one exemplary embodiment of the disclosure, the solid porous structure extends from the outer surface to a depth of 2 mm, typically to a depth of 3 mm, more typically to a depth of 5 mm, more typically to a depth of 10 mm.

The production of a porous structure may be more expensive than the production of a compact structure. Therefore, an applicator in which a solid porous structure is formed only to one depth region may be more cost-effective.

In one exemplary embodiment of the disclosure, the applicator is rotationally symmetrical.

A rotationally symmetrical applicator may be produced cost-effectively as a turned part.

In one exemplary embodiment of the disclosure, the applicator is made as one piece.

A one-piece configuration is cost-effective and easy to handle and can be mounted quickly and simply on the X-ray irradiation device.

In one exemplary embodiment of the disclosure, the applicator is configured in multiple parts.

A multi-part configuration affords the possibility of forming more complex shapes of an applicator. It is conceivable that an applicator can be assembled in a modular system from two or more compatible individual elements. Multi-part applicators that form specific shapes can reduce the treatment time in a tissue by providing optimized distribution of radiation.

In one exemplary embodiment of the disclosure, the whole applicator body has a solid porous structure.

The applicator can therefore be made uniformly from a solid porous material. A volumetric air flow is substantial, since air channels are formed in the whole of the applicator body. An inner cavity of the applicator can also form an air channel.

In one exemplary embodiment of the disclosure, an applicator system includes an applicator and an elastic sterile sleeve, which can be arranged on the outer surface of the applicator.

In this exemplary embodiment of the disclosure, an elastic sterile sleeve is arranged on the outer surface of the applicator. The applicator and the sterile sleeve thus form a system that includes the applicator and the sterile sleeve.

A sterile sleeve is made of a sterile, elastic and radioparent material and can be pulled over the outer surface of the applicator. The sterile sleeve is biocompatible and is suitable for direct contact with tissue. When the air is aspirated at the proximal end of the applicator, the air can flow from each surface region of the outer surface to the proximal end of the applicator through the solid porous surface structure of the applicator. In this way, a vacuum is formed between the sterile sleeve and the outer surface of the applicator, such that the sterile sleeve is fixed to the applicator with form-fit engagement, i.e., no air bubbles remain between the sterile sleeve and the outer surface of the applicator. As a result, deviations from the prescribed irradiation geometry can be avoided during treatment, so that very precise predictions and specifications of the radiation dose acting on the body tissue to be treated are possible. The applicator can also have undercuts. As a result of the aspiration or the vacuum formation, the sterile sleeve is pulled reliably and with form-fit engagement onto the applicator geometry of the outer surface.

The applicator can have any desired outer contour, wherein the contour has no pointed or sharp contour regions, so as to effect a uniform irradiation of a body tissue and so as not to damage the sterile sleeve arranged on the applicator.

The applicator has a shaping function because the applicator has the solid porous structure, i.e., is rigid and thereby shape-retaining, and the sterile sleeve forms the sterile barrier between the applicator and the body tissue. The sterile sleeve can be configured as a low-cost disposable article and can be discarded after use. The applicator does not have to be sterilized and can be used as often as necessary. The temperature demands on the applicator are thus lower.

In one exemplary embodiment of the disclosure, the sterile sleeve has a wall thickness of between 0.05 mm and 1 mm.

A sterile sleeve in this case can be elastic and flexible.

In one exemplary embodiment of the disclosure, the openings or pores of the porous structure have a greatest dimension that is smaller than or equal to the wall thickness of the sterile sleeve.

This reliably prevents any appreciable indenting of the sterile sleeve during the aspiration of the sterile sleeve on the applicator.

In one exemplary embodiment of the disclosure, a channel structure on the outer surface of the applicator has a channel width that is smaller than or equal to the wall thickness of the sterile sleeve.

This reliably prevents any appreciable indenting of the sterile sleeve during the aspiration of the sterile sleeve on the applicator.

In one exemplary embodiment of the disclosure, openings or channels of a porous structure on the outer surface of the applicator have a greatest dimension that is in a range of between 0.1 mm and 1 mm.

This reliably prevents any appreciable indenting of the sterile sleeve during the aspiration of the sterile sleeve on the applicator.

In one exemplary embodiment of the disclosure, a support ring is arranged at an opening of the sterile sleeve.

Advantageously, the sterile sleeve can be easily pulled on over the applicator. The support ring moreover forms a possibility of securing to the irradiation device. The support ring forms a further seal relative to the irradiation device. The sterile sleeve forms, with the irradiation device, a continuous sterile barrier.

In one exemplary embodiment of the disclosure, an X-ray irradiation device includes an applicator, wherein the X-ray irradiation device has a vacuum pump.

An X-ray irradiation device is an irradiation device. A vacuum pump provides the suction power for aspiration of the sterile sleeve on the applicator. The irradiation device with an applicator and with a sterile sleeve can thus be set up conveniently and quickly for use. A vacuum pump can advantageously be used in a suction mode and a pressure mode.

In one exemplary embodiment of the disclosure, maskings are arranged on the applicator.

Maskings can be individually arranged in a non-sterile manner under the sterile sleeve in order to permit targeted delivery of an anisotropic radiation dose. This can reduce treatment times and more precisely control the radiation exposure and also reduce the radiation exposure of other tissue regions.

In one exemplary embodiment of the disclosure, shields are arranged on the applicator.

Shields advantageously reduce side effects on a patient, since tissue regions can be protected from radiation. Shields do not have to be sterile, since they can be arranged under the sterile sleeve.

In one exemplary embodiment of the disclosure, shields are arranged on the applicator in the shaft region.

Advantageously, possible radiation-induced side effects on a patient can be reduced in this region. The shields can be arranged under the sterile sleeve and therefore do not need to be sterile.

In one exemplary embodiment of the disclosure, the applicator can be produced by a 3D printer.

Advantageously, all possible contours and geometries of the applicator can be produced. Channels can advantageously be integrated in the applicator body. The channels can have different shapes and cross sections at different places. Special applicators for individual cases can be produced quickly and cost-effectively.

In one exemplary embodiment of the disclosure, additional cooling channels are arranged in the applicator.

This is advantageous for use in a tissue region and decreases the danger of temperature-induced damage of the tissue.

A method for applying a sterile sleeve to an applicator, which is arranged on an X-ray irradiation device with a vacuum pump, includes:

pulling the sterile sleeve over the applicator, controlling the vacuum pump in a pumping mode, such that air flows through the outer surface of the applicator into the sterile sleeve, positioning the sterile sleeve on the applicator, controlling the vacuum pump in a vacuum mode, such that air is aspirated through the outer surface of the applicator from the sterile sleeve, such that the sterile sleeve bears firmly on the outer surface.

This method makes it easier to arrange a sterile sleeve on an applicator, with air first of all being blown into the sterile sleeve such that the sterile sleeve is inflated like a balloon. In this situation, there is barely any friction between the applicator and the sterile sleeve, such that fold formation and overlaps are reduced and the sterile sleeve can be easily positioned. Thereafter, the vacuum pump changes to a suction mode, such that the air is aspirated from the sterile sleeve, and the latter bears snugly and firmly on the outer surface of the applicator. The sterile sleeve can bear uniformly on the outer surface, since no regions of the sterile sleeve are strongly extended or compressed. The vacuum pump is configured to be used alternately in a pressure mode or in a vacuum mode.

For removal of a sterile sleeve from the applicator, the vacuum pump can be controlled again in a pumping mode, such that air flows through the outer surface of the applicator into the sterile sleeve, and the latter can be easily pulled off from the applicator and removed.

BRIEF DESCRIPTION OF THE DRAWINGS

The disclosure will now be described with reference to the drawing wherein:

FIG. 1 shows a sectional view of an applicator for intraoperative radiotherapy with a highly elastic sterile sleeve according to an exemplary embodiment of the disclosure.

DESCRIPTION OF EXEMPLARY EMBODIMENTS

A radiotherapy system 100 includes an X-ray irradiation device 20 with a receiving stub 27. A tube 30 is arranged in the receiving stub 27. A closure piece (not shown) is arranged at the distal end of the tube 30. The inner face of the closure piece is coated with a radiation medium 31, configured as a gold target. The X-ray irradiation device 20 includes an electron beam source (not shown) which emits an electron beam along a central axis 7. The electron beam strikes the radiation medium 31, i.e., the gold target, with a kinetic energy of at most 100 keV, in one exemplary embodiment 50 keV, such that X-ray radiation is generated with great efficiency at the site of the radiation medium 31. The distal end of the tube 30 thus forms a low-energy X-ray source. The tube 30 can be made from stainless steel.

The electron beam striking the distal end of the tube 30 generates the X-ray radiation isotropically, i.e., with the same intensity in all spatial directions. The radiation intensity is greatest at the distal end of the tube 30 and decreases as the distance from the distal end of the tube 30 increases.

An applicator 1 with an applicator body 5 is arranged on the receiving stub 27. The applicator 1 is pushed onto the receiving stub 27, with a receiving device 8 which is formed by a guide opening, and lies with its proximal end 2 on the contact face 21 of the X-ray irradiation device 20. An inner recess 9, or an inner cavity of the applicator 1, is configured in such a way that the tube 30 of the X-ray irradiation device 20 can be accommodated therein. The inner recess 9 has a cylindrically configured guide opening at the distal end 2 of the applicator 1. In its further course, the inner recess 9 is shaped conically and opens into a cylindrical region 6 in which the distal end of the tube 30 is arranged.

The size and shape of the applicator 1 defines the distance between the radiation medium 31, which forms a radiation source at the distal end of the tube 30, and a tissue that is to be irradiated. The distance of the tissue from the radiation medium 31 is defined by the applicator, such that a desired and/or uniform radiation dose reaches the tissue.

The applicator 1 is configured rotationally symmetrically about the central axis 7. The radiation medium 31 is arranged on the central axis 7 in a central region of the applicator 1 that is provided to be introduced into a body opening. A distal end 3 of the applicator can be inserted into a tissue region (not shown) of a person who is to be treated, as far as a depth that is dependent on the particular use.

The applicator has an outer surface 4. The outer surface 4 is defined by the surface at the circumference and at a distal end 3. A sterile sleeve 10 is arranged over the outer surface 4. The sterile sleeve 10 is made of a sterile, elastic and radioparent material and is suitable for direct contact with tissue. The sterile sleeve 10 and the applicator 1 form two separable parts.

A support ring 11 is arranged at the opening side of the sterile sleeve 10. The support ring 11 forms a seal between the sterile sleeve 10 and the contact face 21 of the X-ray irradiation device 20. The applicator 1 is thus completely enclosed by the contact face 21 and the sterile sleeve 10 with the support ring 11. The applicator 1 here has a shaping function by its rigid shape, and the sterile sleeve 10 forms a sterile barrier between the applicator 1 and a body tissue. The rigid shape of the outer surface 4 of applicator 1 ensures that the outer surface is permanently arranged at a predefined distance from the radiation medium 31 and also has a fixed geometry. This in turn results in a predefined fixed irradiation geometry and the body tissue adjacent to the outer surface is exposed exactly to the radiation dose measured or calculated before the treatment and the radiation treatment can therefore be carried out very precisely.

The outer surface 4 of the applicator 1 forms a solid porous surface structure with holes, cavities and/or channels. The holes, cavities and/or channels form a branched system of multiple air channels, which are connected in an air-conducting manner to the proximal end 2 of the applicator 1. In this way, an air stream can be formed from each region of the outer surface 4 to the proximal end of the applicator. The air stream can be in both directions, either from the outer surface 4 to the proximal end 2 or, conversely, from the proximal end 2 to the outer surface 4.

A first air channel 22 and a second air channel 23 are arranged on the contact face 21 of the X-ray irradiation device 20. The first air channel 22 is connected in an air-conducting manner to a third air channel 24. The second air channel 23 is connected in an air-conducting manner to a fourth air channel 25. The third air channel 24 is attached in an air-conducting manner to the fourth air channel 25 via a connection that is not visible in the sectional view. The fourth air channel 25 is attached to a vacuum pump (not shown). The air stream through the fourth air channel is indicated schematically by a double arrow 26.

The solid porous structure on the outer surface 4 of the applicator 1 is connected in an air-conducting manner to the proximal end 2 of the applicator 1. The vacuum pump, the first air channel 22, the second air channel 23, the third air channel 24 and the fourth air channel 25 thus form an air suction system or an air blow-out system for the applicator 1.

When the air is aspirated at the proximal end of the applicator by this suction system, the air can flow from each surface region of the outer surface 4 to the proximal end 2 of the applicator 1 through the porous surface structure of the applicator 1. In this way, a vacuum is formed between the sterile sleeve 10 and the outer surface 4 of the applicator 1, such that the sterile sleeve 10 is fixed to the applicator 1 with form-fit engagement. The applicator 1 can also have undercuts. By the suction, the sterile sleeve 10 is pulled reliably and with form-fit engagement onto the outer geometry of the applicator 1. In other words, the porous surface structure of applicator 1 is shaped in such a way that there are no isolated surface areas from which the air is not extracted in order to cause air bubbles to remain. The suction of the sterile envelope 10 through the porous structure of the outer surface 4 thus also contributes to the fact that the body tissue can be exposed to a precisely defined radiation dose. If air bubbles remained between the sterile envelope 10 and the outer surface 4, this would have an influence on the irradiation geometry, in particular on the distance between the radiation medium 31 and the body tissue and thus on the radiation dose in the area of the body tissue. The air bubbles could therefore cause deviations from the predicted radiation dose even in the case of a rigid outer surface 4.

The suction power of pressure output of the vacuum pump can be set variably and regulated. In one exemplary embodiment, a pressure sensor (not shown) can be arranged in an air channel. It is possible to define a suction power or a pressure $p0$ up to which a slight suction effect is provided for the sterile sleeve 10, such that the sterile sleeve 10 can be oriented with form-fit engagement on the applicator 1, for example in order to prevent formation of folds or overlaps. The vacuum pump can also be switched off after the pressure $p0$ is reached.

When the sterile sleeve 10 is oriented optimally, the pressure can be further reduced in order to reliably ensure a defined bearing of the sterile sleeve 10 on the applicator 1. Thereafter, the suction power of the vacuum pump can be switched off or reduced to a value which compensates for possible air leakages, such that the tight form-fit engagement of the sterile sleeve 10 is reliably ensured throughout the entire period of use in a tissue region.

It is also possible to define a pressure $p1$ at which the vacuum pump is switched to a pressure mode such that, by air being blown into the applicator 1, a slight pressure is exerted on the sterile sleeve 10. The sterile sleeve 10 is inflated slightly and can thus be oriented with particularly low friction on the applicator 1. Thereafter, the vacuum pump can be switched to a suction mode. The pressure can be reduced in order to reliably ensure aspiration and defined engagement of the sterile sleeve 10 on the applicator 1. Thereafter, the suction power of the vacuum pump can be switched off or reduced to a value that compensates for possible air leakages.

In one exemplary embodiment, the outer surface 4 is formed, to a defined depth, by a solid porous structure with fine holes, cavities and/or channels. The depth can be in a range of between 1 mm and 10 mm.

In one exemplary embodiment, the entire applicator body 5 is made of a solid porous structure with fine holes, cavities and/or channels.

In one exemplary embodiment, one or more additional air-conducting channels with a cross section greater than 1 $mm^2$ are formed in the body of the applicator 1 and run from the proximal end 2 to one or more locations of the porous structure of the outer surface 4.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS 100 radiotherapy system
1 applicator
2 proximal end of the applicator
3 distal end of the applicator
4 outer surface
5 applicator body
6 cylindrical region of the inner recess
7 central axis
8 receiving device
9 inner recess
10 sterile sleeve
11 support ring
20 X-ray irradiation device
21 contact face
22 first air channel
23 second air channel
24 third air channel
25 fourth air channel
26 double arrow
27 receiving stub
30 tube
31 radiation medium

What is claimed is:

1. An applicator system for intraoperative radiotherapy with low-energy X-ray radiation, the applicator system comprising:
    an applicator including:
        an applicator body,
        a proximal end,
        an air-permeable outer surface having a circumferential outer face and defining a distal end of the applicator,
        a receiving device arranged at the proximal end and with which the applicator is securable to an X-ray irradiation device, and
        an inner recess having an opening at the proximal end and into which an X-ray radiation source is insertable,
    the applicator having a solid porous structure on the air-permeable outer surface providing the air-permeable outer surface with a rigid shape, and
    the solid porous structure forming a continuous air-permeable channel structure connected in an air-conducting manner to the proximal end; and
    an elastic sterile sleeve fixed to the applicator on the air-permeable outer surface by a vacuum between the elastic sterile sleeve and the air-permeable outer surface of the applicator.

2. The applicator system according to claim 1, wherein the solid porous structure is formed by a fine channel structure arranged on the air-permeable outer surface.

3. The applicator system according to claim 1, wherein the applicator further comprises channels running from the proximal end to the air-permeable outer surface, and
    wherein the channels are arranged inside the applicator body such that the air-permeable outer surface is connected in the air-conducting manner to the proximal end.

4. The applicator system according to claim 1, wherein the applicator body has entirely the solid porous structure.

5. The applicator system according to claim 1, wherein the elastic sterile sleeve has a wall thickness in a range of between 0.05 millimeters and 1 millimeter.

6. The applicator system according to claim 5, wherein:
    the solid porous structure is formed by a fine channel structure arranged on the air-permeable outer surface of the applicator, and
    the fine channel structure on the air-permeable outer surface of the applicator has a channel width that is smaller than or equal to the wall thickness of the elastic sterile sleeve.

7. The applicator system according to claim 1, wherein:
    the elastic sterile sleeve has a wall thickness,
    the solid porous structure has openings or pores, and
    the openings or pores have a dimension that is smaller than or equal to the wall thickness of the elastic sterile sleeve.

8. The applicator system according to claim 1, wherein:
    the solid porous structure has openings or channels on the air-permeable outer surface of the applicator, and
    the openings or the channels of the solid porous structure on the air-permeable outer surface of the applicator have a dimension that is in a range of between 0.1 millimeters and 1 millimeter.

9. The applicator system according to claim 1, further comprising a support ring,
    wherein the elastic sterile sleeve has a sleeve opening, and
    wherein the support ring is arranged at the sleeve opening.

10. An X-ray irradiation device, comprising:
    the applicator system according to claim 1; and
    a vacuum pump.

11. A method for applying a sterile sleeve to an applicator arranged on an X-ray irradiation device with a vacuum pump, the method comprising:
    pulling the sterile sleeve over the applicator;
    controlling the vacuum pump in a pump mode such that air flows through an air-permeable outer surface of the applicator into the sterile sleeve;
    positioning the sterile sleeve on the applicator; and
    controlling the vacuum pump in a vacuum mode to aspirate air through the air-permeable outer surface of the applicator from the sterile sleeve such that the sterile sleeve is fixed to the applicator on the air-permeable outer surface by a vacuum between the sterile sleeve and the air-permeable outer surface.

* * * * *